(12) United States Patent
Yoon et al.

(10) Patent No.: US 11,681,357 B2
(45) Date of Patent: Jun. 20, 2023

(54) SYSTEMS, DEVICES, AND METHODS FOR PERFORMING AUGMENTED REALITY RESPONSIVE TO MONITORING USER BEHAVIOR

(71) Applicant: Battelle Energy Alliance, LLC, Idaho Falls, ID (US)

(72) Inventors: SuJong Yoon, Idaho Falls, ID (US); Jeffery A. Aguiar, Salt Lake City, UT (US); Johanna H. Oxstrand, Idaho Falls, ID (US); Katya L. Le Blanc, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 17/250,895

(22) PCT Filed: Oct. 2, 2019

(86) PCT No.: PCT/US2019/054187
§ 371 (c)(1),
(2) Date: Mar. 22, 2021

(87) PCT Pub. No.: WO2020/072576
PCT Pub. Date: Apr. 9, 2020

(65) Prior Publication Data
US 2021/0341991 A1     Nov. 4, 2021

Related U.S. Application Data

(60) Provisional application No. 62/741,359, filed on Oct. 4, 2018.

(51) Int. Cl.
*G06F 3/01* (2006.01)
*H04W 4/80* (2018.01)
(Continued)

(52) U.S. Cl.
CPC .......... *G06F 3/011* (2013.01); *A61B 5/02438* (2013.01); *G06F 3/017* (2013.01);
(Continued)

(58) Field of Classification Search
CPC .......... G06F 3/011; G06F 3/017; G06F 1/163; G06F 3/014; G06F 3/0304;
(Continued)

(56) References Cited

U.S. PATENT DOCUMENTS 9,645,652 B2    5/2017  Kelsey et al.
2003/0095140 A1*  5/2003  Keaton ................... G06F 3/042
                                         715/700
(Continued)

FOREIGN PATENT DOCUMENTS

WO    2017/103004 A1    6/2017

OTHER PUBLICATIONS

Doloitte Development LLP, "Augmented reality applications in nuclear power plants," https://www2.deloitte.com/content/dam/Deloitte/us/Documents/process-and-operations/US-cons-augmented-reality-applications-in-nuclear-power-plants.pdf. Copyright 2017, 13 pages.

(Continued)

*Primary Examiner* — Maurice L. McDowell, Jr.
(74) *Attorney, Agent, or Firm* — TraskBritt

(57) ABSTRACT

Systems, devices, and methods are described for performing augmented reality (AR) to assist user performing a task in an environment. An AR device may be configured to capture real-time data. An AR engine may be configured to monitor user behavior from the real-time data responsive to feature extraction from the real-time data, compare the user behavior to pre-defined work procedures, and generate augmented reality objects to be output by the AR device.

22 Claims, 4 Drawing Sheets

(51) Int. Cl.
*A61B 5/024* (2006.01)
*G06Q 10/0631* (2023.01)
*G06V 20/20* (2022.01)
*G06V 40/20* (2022.01)

(52) U.S. Cl.
CPC ..... *G06Q 10/063114* (2013.01); *G06V 20/20* (2022.01); *G06V 40/20* (2022.01); *H04W 4/80* (2018.02)

(58) Field of Classification Search
CPC ....... A61B 5/02438; G06Q 10/063114; G06V 20/20; G06V 40/20; H04W 4/80; H04L 67/131; H04L 67/535
See application file for complete search history.

(56) References Cited

U.S. PATENT DOCUMENTS

| | | | | |
|---|---|---|---|---|
| 2006/0073449 | A1* | 4/2006 | Kumar | F41A 33/00 434/226 |
| 2012/0075343 | A1* | 3/2012 | Chen | G06T 19/006 345/633 |
| 2014/0277596 | A1* | 9/2014 | Nixon | G05B 11/01 700/17 |
| 2014/0359540 | A1* | 12/2014 | Kelsey | G06F 3/017 715/863 |
| 2016/0295038 | A1* | 10/2016 | Rao | H04W 40/02 |
| 2018/0190028 | A1* | 7/2018 | Wadley | G06V 20/20 |
| 2018/0225993 | A1* | 8/2018 | Buras | A61B 34/20 |
| 2019/0325660 | A1* | 10/2019 | Schmirler | G06F 3/011 |
| 2019/0332751 | A1* | 10/2019 | Brady | G06F 21/40 |

OTHER PUBLICATIONS

International Search Report from International Application No. PCT/US2019/054187, dated Jan. 2, 2020, 2 pages.

International Written Opinion from International Application No. PCT/US2019/054187, dated Jan. 2, 2020, 4 pages.

Ishii, et al., "Augmented Reality Applications for Nuclear Power Plant Maintenance Work," ISSNP, International Symposium on Symbiotic Nuclear Power Systems for 21st Century, (2007) pp. 262-268.

* cited by examiner

SYSTEMS, DEVICES, AND METHODS FOR PERFORMING AUGMENTED REALITY RESPONSIVE TO MONITORING USER BEHAVIOR

CROSS-REFERENCE TO RELATED APPLICATIONS

This application is a national phase entry under 35 U.S.C. § 371 of International Patent Application PCT/US2019/054187, filed Oct. 2, 2019, designating the United States of America and published as International Patent Publication WO 2020/072576 A1 on Apr. 9, 2020, which claims the benefit under Article 8 of the Patent Cooperation Treaty to U.S. Patent Application Ser. No. 62/741,359, filed Oct. 4, 2018.

STATEMENT REGARDING FEDERALLY SPONSORED RESEARCH OR DEVELOPMENT

The present disclosure was made with government support under Contract No. DE AC07 05-ID14517 awarded by the United States Department of Energy. The government has certain rights in the present disclosure.

TECHNICAL FIELD

Embodiments of the present disclosure relate generally to systems, devices, and methods for augmented reality wearable technology for monitoring, support, and/or control of nuclear power plants.

BACKGROUND

Human performance is of great importance to the safety, operation, performance and productivity of nuclear power plants. According to the U.S. Department of Energy, approximately 80% of significant events at the nuclear power plants occur due to human error, while approximately 20% are caused by equipment failures. Human error may result from either individual error or organizational error. In order to improve on human performance at nuclear facilities and nuclear power plants, both individual and organizational performances should be properly monitored to help identify the performance gaps that result in human errors.

Computer-based procedures (CBPs) and automated work processes (AWS) have been developed to improve human performance and may reduce the cost and time to complete work by replacing paper-based systems. These solutions often fall short in ensuring detection and prevention of human error in the field because they still rely on worker input. Field activities often cannot be monitored or controlled remotely. Therefore, control room operators, plant engineers, and planners often rely on information gathered from workers to safely monitor and control the plant. There can be large uncertainties and worker bias in information collected in the field because current CBPs still depend on human inputs and utilize work procedures that do not always specify full details of the task. From the plant operation and outage management point of view, the field activity data may be utilized to identify performance gaps.

BRIEF SUMMARY

In some embodiments an augmented reality (AR) system includes an AR device configured to capture real-time data and an AR engine. The AR engine is configured to monitor user behavior from the real-time data responsive to feature extraction from the real-time data, compare the user behavior to pre-defined work procedures, and generate augmented reality objects to be output by the AR device.

In some embodiments a network of augmented reality (AR) systems includes a first AR system and a second AR system. The first AR system includes a first AR device configured to capture first real-time data and a first AR engine configured to monitor first user behavior responsive to the first real-time data. The second AR system includes a second AR device configured to capture second real-time data and a second AR engine configured to monitor second user behavior responsive to the second real-time data. The first user behavior and the second user behavior are compared to pre-defined work procedures in a coordinated manner to coordinate efforts of a first user associated with the first AR system and a second user associated with the second AR system.

BRIEF DESCRIPTION OF THE DRAWINGS

While the specification concludes with claims particularly pointing out and distinctly claiming what are regarded as embodiments of the present disclosure, various features and advantages of embodiments of the disclosure may be more readily ascertained from the following description of example embodiments of the disclosure when read in conjunction with the accompanying drawings, in which:

DETAILED DESCRIPTION

Figure 1:
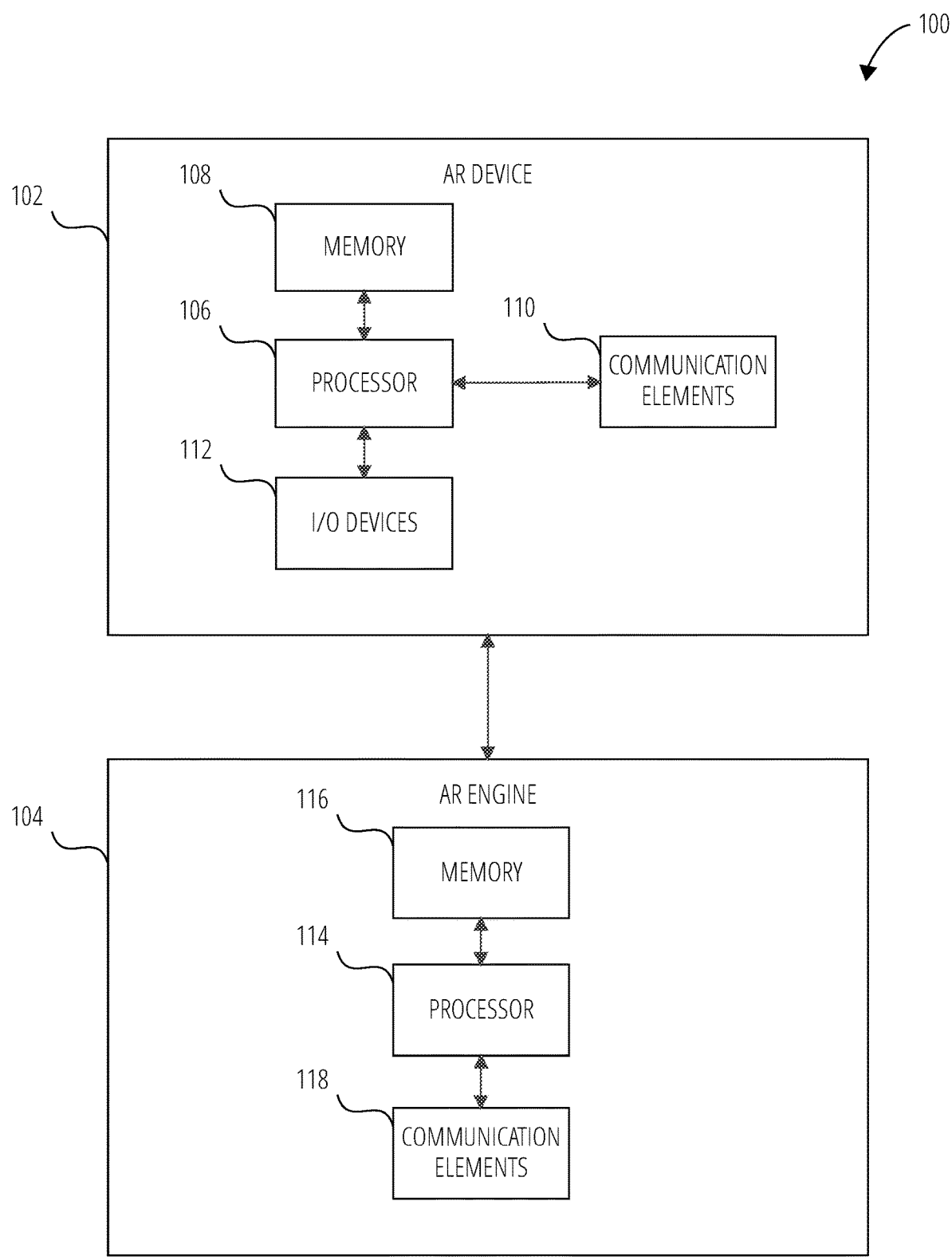
FIG. 1 is an augmented reality (AR) system specifically configured for operation within a nuclear facility according to an embodiment of the present disclosure.

In the following description, reference is made to the accompanying drawings in which are shown, by way of illustration, specific embodiments in which the disclosure may be practiced. The embodiments are intended to describe aspects of the disclosure in sufficient detail to enable those skilled in the art to make, use, and otherwise practice the present disclosure. Furthermore, specific implementations shown and described are only examples and should not be construed as the only way to implement the present disclosure unless specified otherwise herein. It will be readily apparent to one of ordinary skill in the art that the various embodiments of the present disclosure may be practiced by numerous other partitioning solutions. Other embodiments may be utilized and changes may be made to the disclosed embodiments without departing from the scope of the disclosure. The following detailed description is not to be taken in a limiting sense, and the scope of the present disclosure is defined only by the accompanying claims.

In the following description, elements, circuits, and functions may be shown in block diagram form in order not to obscure the present disclosure in unnecessary detail. Conversely, specific implementations shown and described are exemplary only and should not be construed as the only way to implement the present disclosure unless specified otherwise herein. Additionally, block definitions and partitioning of logic between various blocks is exemplary of a specific implementation. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Those of ordinary skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths, and the present disclosure may be implemented on any number of data signals including a single data signal.

The various illustrative logical blocks, modules, and circuits described in connection with the embodiments disclosed herein may be implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A general purpose processor may be considered a special purpose processor while the general purpose processor executes instructions (e.g., software code) stored on a computer readable medium. A processor may also be implemented as a combination of computing devices, e.g., a combination of a DSP and a microprocessor, a plurality of microprocessors, one or more microprocessors in conjunction with a DSP core, or any other such configuration.

Also, it is noted that embodiments may be described in terms of a process that may be depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on computer readable media. Computer readable media include both computer storage media and communication media, including any medium that facilitates transfer of a computer program from one place to another.

It should be understood that any reference to an element herein using a designation such as "first," "second," and so forth, does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. In addition, unless stated otherwise, a set of elements may comprise one or more elements.

The inventors have appreciated that effective collection and utilization of field activity data has a great potential to significantly reduce labor cost and safety challenges. Embodiments of the present disclosure include augmented reality (AR) wearable technology configured to monitor the activities of a user (e.g., field worker) at a nuclear facility (e.g., nuclear power plant). In some embodiments the system may perform various actions responsive to the monitoring such as verifying completion of a particular task, identifying incorrect completion of a task, alerting and/or advising the user of an incorrect action, record related data related to these activities and others performed by the user, and other related actions.

FIG. 1 is an augmented reality system (AR system 100) specifically configured for operation within a nuclear facility according to an embodiment of the present disclosure. The AR system 100 includes an AR device 102 operably coupled with an AR engine 104. In some embodiments the AR device 102 and the AR engine 104 may be remote from each other (e.g., the AR engine 104 incorporated within a remote server). In some embodiments certain features of the AR engine 104 may be incorporated within the AR device 102. In yet other embodiments the AR engine 104 may be completely incorporated within the AR device 102. As a result, remote connectivity may not be required for operation of the AR device 102. Data collected by the AR device 102 may be stored locally and/or periodically transmitted to a remote server for external storage. Communication between remote devices may be performed over a wired and/or wireless network (e.g., Internet, cellular network, etc.).

The AR device 102 may be a mobile and/or wearable device (e.g., glasses, goggles, helmet, attachment device, mobile electronic device such as a smart phone, a tablet computer, etc.). In some embodiment, the AR device 102 may be an AR attachment configured to be mounted on a non-AR device (e.g., a peripheral device) such as the user's normal gloves, clothing, hat, helmet, shoes, glasses or protective eyewear (e.g., goggles) to effectively transform the non-AR device to an AR device. The AR device 102 may be configured to perform interactive visualization of augmented reality that allows users to see virtual objects simultaneously with real objects in a real environment. More particularly, the AR device 102 may display, in real-time, text, video, images or other messages to the user, as well as producing other outputs (e.g., voice, synthesized voice, etc.). The virtual objects may be generated by the AR engine 104 responsive to processing data based on pre-defined work procedures and work instructions. The AR device 102 may also be configured to monitor behavior of the user as will be discussed more fully below.

The AR device 102 may include a processor 106 operably coupled with memory 108, communication elements 110, and one or more different I/O devices 112. The memory 108 may include one or more volatile data storage devices (e.g., random access memory (RAM), etc.), one or more non-volatile data storage devices (e.g., read only memory (ROM), Flash data storage, a hard drive, etc.), or both volatile and non-volatile data storage devices. In some embodiments the processor 106 may be configured to execute computer-readable instructions stored (e.g., permanently and/or temporarily) by the memory 108. The computer-readable instructions may be configured to instruct the processor 106 to control the AR device 102 to perform functions discussed herein that the AR device 102 is configured to perform.

The I/O devices 112 may include input devices configured to collect data (e.g., real-time data) and/or interact with the user. Non-limiting examples of such input devices include motion sensors, biometric sensors, accelerometers, geolocational sensors (e.g., global positioning system (GPS) sensors), image sensors (e.g., still or video cameras), heat sensors, light sensors (e.g., visual spectrum light sensors, non-visual spectrum light sensors), moisture sensors, touch sensors, microphones, biometric sensors (e.g., heartrate monitors), etc. Accordingly, non-limiting examples of data captured by the AR device 102 may include location data (e.g., GPS geolocation data), biometric data (e.g., heartrate data), motion/acceleration data, image/video data, environmental data (e.g., heat data, light data, moisture data, etc.), posture data (e.g., information indicating wherein a user's body a sensor/AR device 102 is located), other data, and any combination thereof.

The I/O devices 112 may also include output devices configured to generate responses to the collected data and/or responsive to the AR engine 104. Non-limiting examples of such output devices may include speakers, display screens (e.g., a rendering screen), projectors, etc. Additional details of an example of an AR device 102 and related system elements is described in PCT Application Publication WO2017103004A1, entitled "Method and Apparatus for Displaying Content in Augmented Reality Settings," filed Dec. 15, 2016 as PCT/EP2016/081287, the disclosure of which is incorporated herein in its entirety by this reference.

The AR engine 104 may include a processor 114 operably coupled with a memory 116 and communication elements 118. The memory 116 may include one or more volatile data storage devices (e.g., random access memory (RAM), etc.), one or more non-volatile data storage devices (e.g., read only memory (ROM), Flash data storage, a hard drive, etc.), or both volatile and non-volatile data storage devices. In some embodiments the processor 114 may be configured to execute computer-readable instructions stored (e.g., permanently and/or temporarily) by the memory 116. The computer-readable instructions may be configured to instruct the processor 114 to control the AR engine 104 to perform functions discussed herein that the AR engine 104 is configured to perform.

The AR engine 104 may be configured to perform deep machine learning to monitor, process, and predict field activity without human-input. For example, learning-based neural network models for the object detection and action recognition may be performed on video data captured by the AR device 102. Such learning based algorithms may be configured to automatically perform the feature extraction from the data, through interconnected neural networks making up highly deterministic encoders and decoders of the data.

In cooperation with the AR engine 104, the AR device 102 may provide an advanced human-machine-interface configured to utilize synchronized sensors with the electronic display to support augmented reality projection to the user. More particularly, the AR device 102 and AR engine 104 may be configured to monitor and support users and their activities at nuclear facilities for providing work instructions and other activities in real-time. In other words, the users may be presented with information generated by the AR engine 104 responsive to the data collected by the sensors of the AR device 102. The AR information provided to the user may improve safety and performance by freeing their hands.

In some embodiments the information presented to the user may also be shared with other parties, such as control room operators who may also communicate with the users over an established communication channel between the control room devices and the AR device 102. The AR engine 104 may be configured to automatically generate efficient directions to the users involved in routine and complex operations responsive to processing the data collected by the AR device 102, which may also be supplemented by the shared vision of the control room operators.

The AR device 102 and AR engine 104 may be configured to monitor the behavior and actions of the field worker in a nuclear facility. For example, the sensors (e.g., video camera) on the AR device 102 may capture data indicative of the user's movements. The data may be processed by the AR engine 104 to analyze the motion of the user directly from the video images or other sensor data of the AR device 102 itself. Prior to operation, the AR engine 104 may be provided with a well-characterized set of videos or other data that may be collected from a similar laboratory setting to provide a baseline for the AR system 100 and for developing the deep learning techniques. Full data sets may be captured, which may be quantified and processed using deep learning.

As a non-limiting example, the user may be required to perform a task of turning a valve to a certain degree. The AR device 102 may capture the image data (e.g., video) showing the user turning the valve. The image data may be sent to the AR engine 104 to perform image processing (e.g., gesture recognition) to verify that the valve was turned to the degree required for that task. The image processing may extract gestures related to the body movements (e.g., hands) of the user, by focusing on the motion of the tools (e.g., wrench) utilized by the user to perform the task, by focusing on the motion of the component being acted upon (e.g., the valve), and combinations thereof.

Continuing with the valve example, different valves may be required to be turned different degrees. As a result, the AR device 102 may capture geolocational data that the AR engine 104 may use to determine where the user is, what task is to be performed at that location, and what the requirements are for that task before performing the monitoring of the user's actions. In some embodiments the AR engine 104 may send the task instructions to the AR device 102 to present the task information to the user. If the task is determined to have been completed accurately, the AR engine 104 may send a notification to the AR device 102 to inform the user of such. If, however, the task is determined to not have been completed accurately, the AR engine may send an alert to the AR device 102 to provide real-time feedback indicating that the task was not correct and, in some cases, present the corrective action and/or a reminder of the task requirements through the AR device 102. In some embodiments the component status information may be provided to the AR device 102 before and/or after the task is performed by the user. In some embodiments the sensor data may be analyzed by the AR engine 104 to perform learning-based failure predictions generated from signal patterns of diagnostic sensor data.

As another non-limiting example, the user may be required to perform a pre-defined task and the I/O devices 112 may include a heartrate monitor configured to monitor a heartrate of the user. Where the monitored heartrate of the user exceeds a predetermined threshold value, the AR engine 104 may be configured to determine that a problem has occurred or that the user should pause in performance of the pre-determined task to calm down (e.g., where fine, precise actions are needed or a steady had is otherwise helpful in performing the pre-defined task). For example, the user may be contacted by another person (e.g., a manager) of the nuclear power facility to inquire whether everything is okay or if assistance is needed. As another example, the user may be instructed to continue performance of the pre-determined task responsive to the detected heartrate of the user falling into an acceptable range of values.

In some embodiments work procedures may be refined (e.g., by the AR engine 104) over time based on data collected by the AR device 102 (e.g., using reinforcement learning). For example, one or more users may perform a certain pre-defined task associated with a pre-defined work procedure multiple times over the course of an extended period of time (e.g., an hourly task, a daily task, a weekly task, etc.). The AR engine 104 may recognize, based on the data collected by the AR device 102, variations in how the pre-defined task is performed at different times. The AR engine 104 may associate certain nuances of human behavior in performing the pre-defined task with better completion of the pre-defined task and other nuances of human behavior with performing the pre-defined task with poorer completion of the pre-defined task. The better and poorer completion may be measured with respect to a successful completion rate of the pre-defined task, speed, safety, and/or efficiency (e.g., time efficiency, cost efficiency, etc.) of performance of the pre-defined task, other metric, or combinations thereof (e.g., using an optimization of a cost function or objective function involving multiple different metrics). As a non-limiting example, a work procedure may include a pre-defined task involving a user turning a valve. Over time, some instances of the user turning the valve may involve the user's use of a single hand in turning the valve, and other instances of the user turning the valve may involve the user's use of both hands in turning the valve. If it is observed by the AR engine 104 over time that the user is more likely to perform the turning of the valve successfully or more efficiently when two hands are used the AR engine 104 may modify the pre-defined work procedure to advise or require the use of both hands to turn the valve in completing the pre-defined procedure.

As a result, the improvements to the AR device 102, the AR engine 104, and the AR system 100 generally, may also result in an improvement on the operation of the nuclear facility. For example, because of the improved features performed by the AR system 100, individual human errors at the nuclear facility may be reduced, the elapsed time per task may be reduced, etc. In addition, detailed field activity logs may be generated and various work tasks validated and recorded, which may further improve safety. By incorporating these features at the AR device 102, embodiments of the disclosure may reduce (or eliminate) a number of motion sensors or cameras that may be mounted around the nuclear facility.

Figure 2:
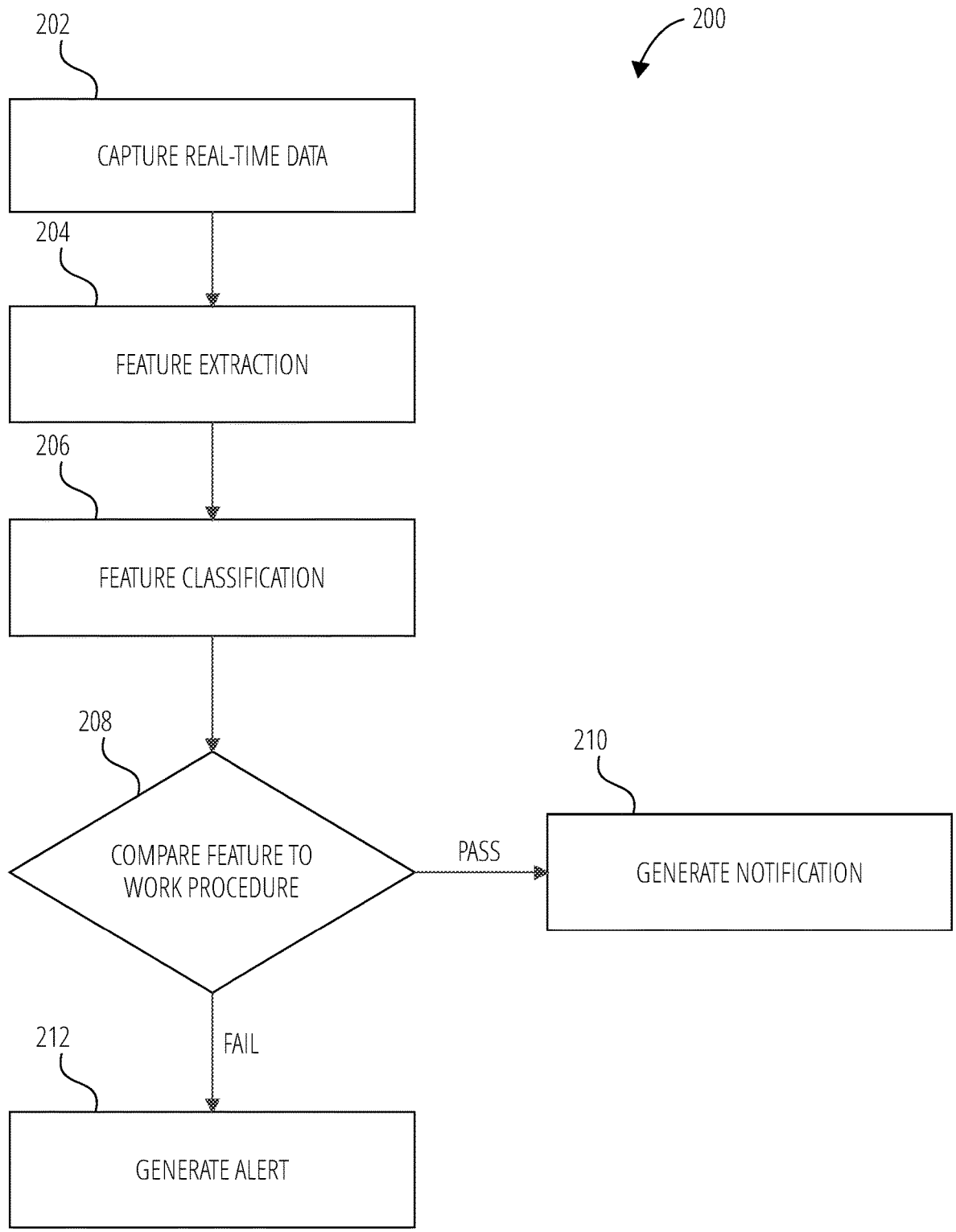
FIG. 2 is a flowchart illustrating a method of operating an augmented reality system according to an embodiment of the disclosure.

FIG. 2 is a flowchart illustrating a method 200 of operating an AR system according to an embodiment of the disclosure. At operation 202, real-time data may be captured by the AR device. The real-time data may include a video data stream from a camera incorporated within the AR device and/or other data that may be utilized by the AR engine. For a video data stream, the AR device may capture multiple frames at a time to process and analyze. At operation 204, the feature extraction may be performed from the real-time data (e.g., by a neural network). The AR engine may include different feature datasets (e.g., a hand gesture data set, a tool data set, a component data set, or combinations thereof). The feature datasets may be pre-populated and validated during training of the AR system. At operation 206, the feature may be classified according to the classification databases also pre-populated and validated during training. At operation 208, the analyzed features may then be compared to the particular pre-defined work procedure or task being performed by the user. If the procedure was correct, the AR engine may generate a notification at operation 210. If the procedure was not correct, the AR engine may generate an alert at operation 212. The results may also be stored by the AR system for future reference or for further adaptive improvements to the training databases.

Although examples herein are described within the context of the nuclear industry and nuclear facilities, embodiments of the disclosure may also include other applications and industries that may include labor-intensive tasks. For example, embodiments of the disclosure may be incorporated into applications such as machine (e.g., HVAC) installation and repair or for other types of applications within plants or factories. For nuclear applications, the field activity data generated by the disclosed system may be utilized by the work organization so that the capacity rate of the nuclear power plant is increased. In addition, deep learning applications for systems and components diagnostics may reduce unplanned maintenance through accurate prediction of system failures. For long-term prospects, the learning-based artificial intelligence (AI) applications may be integrated with robotics platforms so that the AI robots may be deployed into the nuclear facility not only for automated operation and maintenance, but also for emergency activities following severe accidents. As a result, the cost of the severe accident settlement may be reduced.

Figure 3:
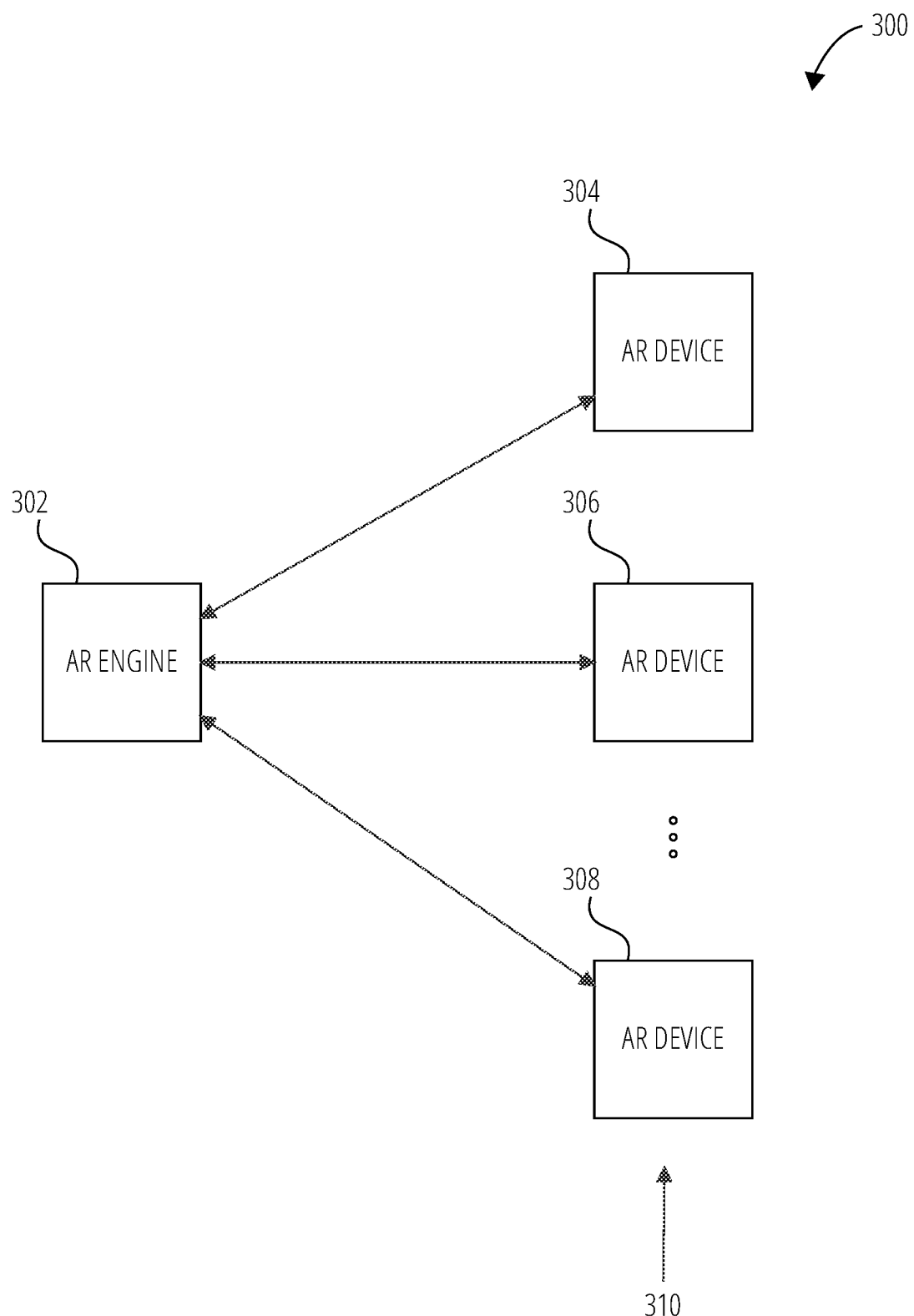
FIG. 3 is a block diagram of an AR system, according to some embodiments.

FIG. 3 is a block diagram of an AR system 300, according to some embodiments. The AR system 300 includes an AR engine 302 similar to the AR engine 104 of FIG. 1. The AR system 300 also includes multiple AR devices 310 (e.g., AR device 304, AR device 306, and AR device 308), each similar to the AR device 102 of FIG. 1, operably coupled to the AR engine 302. As a result, the AR engine 302 is configured to monitor user behavior responsive to feature extraction from data (e.g., real-time data) collected by the AR devices 310. The AR engine 302 is also configured to compare the user behavior to pre-defined work procedures and generate augmented reality objects (e.g., alarms, corrective instructions, indications that the work procedures were successfully completed, etc.) to be provided via the AR devices 310.

In some embodiments each of the AR devices 310 operably coupled to the AR engine 302 may collect data associated with a single user's performance of tasks of a pre-defined procedure. By way of non-limiting example, the AR device 304 may include a pair of glasses (e.g., including a video camera), the AR device 306 may include a helmet (e.g., including a biometric sensor), and the AR device 308 may include a glove (e.g., having sensors to collect data regarding various hand positions and/or hand gestures). A single user may wear the glasses, the helmet, and the glove. As the user performs the task, the AR device 304, the AR device 306, and the AR device 308 may each provide data to the AR engine 302.

In some embodiments the AR devices 310 may be associated with more than one user (e.g., each user has at least one of the AR devices 310 associated therewith). In this way, coordinated efforts of multiple users may be coordinated by the AR engine 302. Accordingly, a work procedure involving tasks of multiple different workers may be coordinated through the AR engine 302, which may provide feedback, via the AR devices 310, to each of the users involved in the work procedure.

Figure 4:
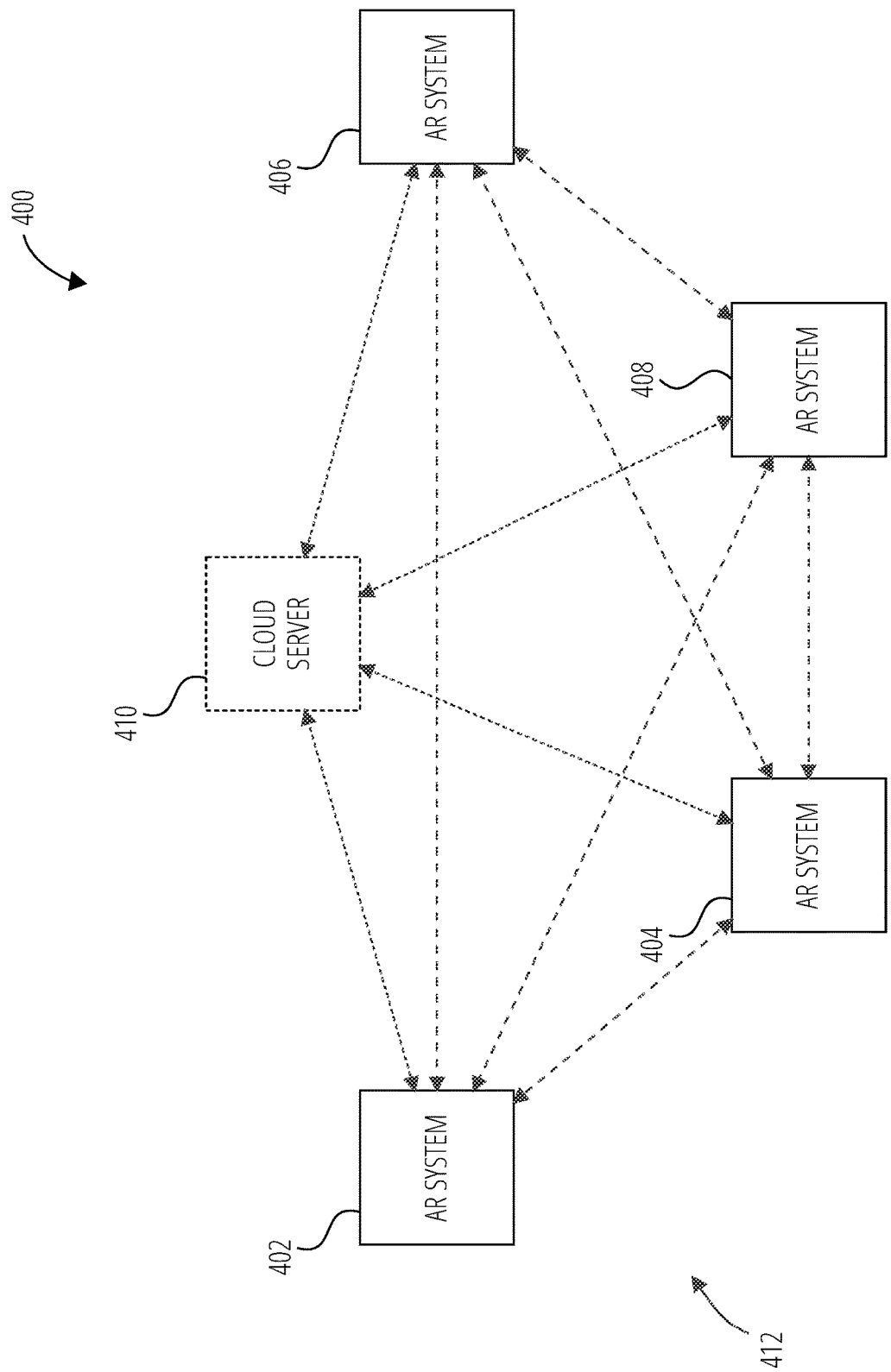
FIG. 4 is a block diagram of a network of AR systems, according to some embodiments.

FIG. 4 is a block diagram of a network 400 of AR systems 412 (e.g., AR system 402, AR system 404, AR system 406, AR system 408), according to some embodiments. Each of the AR systems 412 may be similar to the AR system 100 of FIG. 1 and/or the AR system 300 of FIG. 3. For example, each of the AR systems may include one or more AR devices (e.g., similar to the AR device 102 of FIG. 1 and/or the AR device 304, AR device 306, and AR device 308 of FIG. 3) configured to capture data (e.g., real-time data) and an AR engine (e.g., similar to the AR engine 104 of FIG. 1 and/or the AR engine 302 of FIG. 3) configured to monitor user behavior responsive to the captured data. In some embodiments the AR systems 412 may be associated with multiple users (e.g., one or more users associated with each one of the AR systems 412). Behaviors of multiple users, as determined from the data captured by the AR devices, are compared to pre-defined work procedures in a coordinated manner to coordinate efforts of the multiple users.

In some embodiments the AR engines of the AR systems 412 are configured to work together to coordinate pre-defined work procedures. In such embodiments the communication elements (e.g., the communication elements 118 of FIG. 1) of the AR systems may be configured to communicate with each other (indicated in FIG. 400 using dashed lines). By way of non-limiting example, the AR systems 412 may be configured to communicate with each other wirelessly (e.g., using a near field communication (NFC) protocol such as BLUETOOTH®, using Wi-Fi, using ZIGBEE®, using cellular data communications, etc.). In some embodiments the AR systems 412 may be configured to communicate with each other in a mesh network configuration (e.g., the AR systems 412 may communicate with each other and relay communications between others of the AR systems 412). In some embodiments the AR systems 412 may communicate with each other through a server (e.g., a cloud server 410, communications between the cloud server 410 and the AR systems 412 indicated with dotted lines).

In some embodiments one of the AR systems 412 may be designated as a master node of the network 400. In such embodiments the captured data from each of the AR systems 412 may be routed to the master AR system, which may compare user behaviors based on the captured data to pre-defined procedures involving the multiple users associated with the network 400. In some embodiments, however, two or more (e.g., all) of the AR systems 412 may collectively act as the master node of the network 400 in a distributed network configuration. In some embodiments the cloud server 410 may serve as the master node of the network 400. In such embodiments the captured data from each of the AR systems 412 may be provided or otherwise routed to the cloud server 410. The cloud server 410 may then compare user behaviors based on the captured data to pre-defined procedures involving the multiple users associated with the network 400.

In some embodiments each of the AR systems 412 may be configured to operate independently from others of the AR systems 412 (e.g., each of the AR systems 412 may be operated independently even without communicating with others of the AR systems 412 or the cloud server 410). Coordination of pre-defined procedures may still be accomplished in such embodiments. For example, timing of certain pre-defined tasks associated with each of the AR systems 412 may be pre-established, and as long as each of the AR systems 412 follows the established timing, the AR systems 412 may effectively coordinate.

EXAMPLES

A non-exhaustive, non-limiting list of example embodiments follows. Not each of the example embodiments listed below is individually expressly indicated as being combinable with all others of the example embodiments listed below and embodiments discussed above. It is intended, however, that these example embodiments are combinable with all other example embodiments and embodiments discussed above unless it would be apparent to one of ordinary skill in the art that the embodiments are not combinable.

Example 1: An augmented reality (AR) system, including: an AR device configured to capture real-time data; and an AR engine configured to: monitor user behavior from the real-time data responsive to feature extraction from the real-time data; compare the user behavior to pre-defined work procedures; and generate augmented reality objects to be output by the AR device.

Example 2: The AR system of Example 1, wherein the AR device is selected from the group consisting of glasses, goggles, a helmet, and an attachment device.

Example 3: The AR system of Example 1, wherein the real-time data includes video data.

Example 4: The AR system of Example 1, wherein the feature extraction includes identifying body gestures of the user.

Example 5: The AR system of Example 1, wherein the feature extraction includes identifying motion of a tool utilized by the user to perform a task defined by the pre-defined work procedures.

Example 6: The AR system of Example 1, wherein the feature extraction includes identifying motion of a component acted upon by the user while performing a task defined by the pre-defined work procedures.

Example 7: The AR system of Example 1, wherein the augmented reality objects include an alert indicative of the user behavior not complying with the pre-defined work procedures.

Example 8: The AR system of Example 7, wherein the alert includes instructions provided to the user to perform corrective action.

Example 9: The AR system of Example 1, wherein the augmented reality objects include a notification indicative of the user behavior complying with the pre-defined work procedures.

Example 10: The AR system of Example 1, wherein the AR engine and the AR device are incorporated within a single housing.

Example 11: The AR system of Example 1, wherein the AR engine and the AR device are located remote from each other.

Example 12: A system at least substantially as shown in the drawing figures and described in the specification.

Example 13: A device at least substantially as shown in the drawing figures and described in the specification.

Example 14: A method at least substantially as shown in the drawing figures and described in the specification.

Although examples herein are described with within the context of the nuclear industry and nuclear facilities, embodiments of the disclosure may also include other applications and industries that may include labor-intensive tasks. For example, embodiments of the disclosure may be incorporated into applications such as machine (e.g., HVAC) installation and repair or for other types of applications within plants or factories. For nuclear applications, the field activity data generated by the disclosed system may be utilized by the work organization so that the capacity rate of the nuclear power plant increased. In addition, deep learning applications for systems and components diagnostics may reduce unplanned maintenance through accurate prediction of system failures. For long-term prospects, the learning-based artificial intelligence (AI) applications may be integrated with robotics platforms so that the AI robots may be deployed into the nuclear facility not only for automated operation and maintenance, but also for emergency activities following severe accidents. As a result, the cost of the severe accident settlement may be reduced.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the present disclosure as hereinafter claimed, including legal equivalents thereof. In addition, features from one embodiment may be combined with features of another embodiment while still being encompassed within the scope of the present disclosure. Further, embodiments of the disclosure have utility with different and various detector types and configurations.

What is claimed is:

1. An augmented reality (AR) system, comprising:
    an AR device configured to capture real-time data; and
    an AR engine including a processor configured to execute computer-readable instructions configured to instruct the processor to:
        monitor user behavior from the real-time data responsive to feature extraction from the real-time data;
        compare the user behavior and another user behavior corresponding to another AR system to pre-defined work procedures in a coordinated manner to coordinate efforts of the user with the other user; and
        generate augmented reality objects to be output by the AR device responsive to the comparison of the user behavior, the other user behavior, and the pre-defined work procedures;
    wherein the generated augmented reality objects are at least partially related to the pre-defined work procedures.

2. The AR system of claim 1, wherein the AR device is selected from the group consisting of glasses, goggles, a helmet, a mobile electronic device, a tablet device, and an attachment device.

3. The AR system of claim 2, wherein the attachment device is configured to attach to a peripheral device.

4. The AR system of claim 3, wherein the peripheral device is selected from the group consisting of glasses, goggles, a helmet, a hat, a glove, a shoe, and clothing.

5. The AR system of claim 1, wherein the real-time data includes video data.

6. The AR system of claim 1, wherein the real-time data includes peripheral sensor data from one or more peripheral sensors of the AR device.

7. The AR system of claim 6, wherein the peripheral sensor data includes biometric sensor data.

8. The AR system of claim 7, wherein the biometric sensor data includes heartrate information of a user of the AR device.

9. The AR system of claim 1, wherein the real-time data includes location data corresponding to a location of the AR device.

10. The AR system of claim 1, wherein the real-time data includes environment data corresponding to environmental conditions proximate to the AR device.

11. The AR system of claim 1, wherein the real-time data includes posture data identifying a posture of the AR device relative to a user of the AR device.

12. The AR system of claim 1, wherein the feature extraction includes identifying body gestures of a user.

13. The AR system of claim 1, wherein the feature extraction includes identifying motion of a tool utilized by a user to perform a task defined by the pre-defined work procedures.

14. The AR system of claim 1, wherein the feature extraction includes identifying motion of a component acted upon by a user while performing a task defined by the pre-defined work procedures.

15. The AR system of claim 1, wherein the augmented reality objects include an alert indicative of the user behavior not complying with the pre-defined work procedures.

16. The AR system of claim 15, wherein the alert includes instructions provided to a user to perform corrective action.

17. The AR system of claim 1, wherein the augmented reality objects include a notification indicative of the user behavior complying with the pre-defined work procedures.

18. The AR system of claim 1, wherein the AR engine is configured to associate an identified human behavior with successful completion of a pre-defined task of a pre-defined work procedure and implement the identified human behavior into the pre-defined work procedure as part of the pre-defined task.

19. A network of augmented reality (AR) systems, the network comprising:
    a first AR system comprising a first AR device configured to capture first real-time data and a first AR engine configured to monitor first user behavior responsive to the first real-time data; and
    a second AR system comprising a second AR device configured to capture second real-time data and a second AR engine configured to monitor second user behavior responsive to the second real-time data, the first AR engine and the second AR engine each including a processor configured to execute computer-readable instructions configured to instruct the processor to perform operations of the respective one of the first AR engine and the second AR engine;
    wherein the first user behavior and the second user behavior are compared to pre-defined work procedures in a coordinated manner to coordinate efforts of a first user associated with the first AR system and a second user associated with the second AR system.

20. The network of claim 19, wherein the first AR system and the second AR system are networked together using a wireless communication protocol.

21. The network of claim 19, wherein the first AR system and the second AR system are networked together using a near-field communication protocol.

22. The network of claim 19, further comprising a cloud server configured to communicate with the first AR system and the second AR system, the cloud server configured to coordinate the efforts of the first user and the second user.

* * * * *